United States Patent [19]

Kim

[11] 4,241,044

[45] Dec. 23, 1980

[54] METHOD OF DIAGNOSING CANCER BY DETECTING ELEVATED ANTI-T ANTIBODY ACTIVITY

[75] Inventor: Yung D. Kim, Lindenhurst, Ill.

[73] Assignee: Abbott Laboratories, North Chicago, Ill.

[21] Appl. No.: 973,991

[22] Filed: Dec. 28, 1978

[51] Int. Cl.$^2$ .................. G01N 33/16; A61K 43/00
[52] U.S. Cl. .................. 424/1; 23/230 B; 260/112 B
[58] Field of Search .................. 424/112; 23/230 B; 260/112 R, 112 B

[56] References Cited

U.S. PATENT DOCUMENTS

| | | | |
|---|---|---|---|
| 3,663,684 | 5/1972 | Freedman et al. | 424/1 |
| 3,697,638 | 10/1972 | Hansen | 424/1 |
| 3,823,126 | 7/1974 | Bjorklund | 260/112 R |
| 3,867,363 | 2/1975 | Hansen | 260/112 R |
| 3,956,258 | 5/1976 | Hansen | 260/112 R |
| 3,960,827 | 6/1976 | Bjorklund | 260/112 R |
| 4,132,767 | 1/1979 | Tohmatsu et al. | 424/1 |
| 4,152,410 | 5/1979 | Ishii | 424/1 |
| 4,160,817 | 7/1979 | Bucovaz et al. | 424/1 |

Primary Examiner—Benjamin R. Padgett
Assistant Examiner—Christine M. Nucker
Attorney, Agent, or Firm—Neal O. Willmann

[57] ABSTRACT

This application discloses a method for diagnosing cancer by employing any of various immunochemical procedures to detect elevated levels of anti-(blood group T antigen) antibodies in a biological sample.

8 Claims, No Drawings

METHOD OF DIAGNOSING CANCER BY DETECTING ELEVATED ANTI-T ANTIBODY ACTIVITY

BACKGROUND OF THE INVENTION

Serum anti-T agglutinins are antibodies having specificity for the cryptic blood group substance known as the Thomsen-Friedenreich T-antigen. The T-antigen has been found in all human sera and in the sera of other mammals such as rabbits and goats. Localized on erythrocytes, T-antigen is considered an immediate biosynthetic precursor of blood group MN antigens, and not expressed under ordinary circumstances. However, MN antigens may be converted in vitro to T-antigen by either an enzymatic or acidic pH treatment [G. F. Springer et al., Carbohydrate Research, 40, 183, (1975)].

A significant level of circulating anti-T agglutinin appears during the first year after birth and by the age of three, it reaches titers found in adult sera [P. E. Lind et al., Australian J. Expl. Biol. Med. Sci., 25, 247, (1947)].

While a normal, healthy adult usually exhibits constant mean anti-T titers, higher than normal titers have been measured in sera from patients exhibiting atypical pneumonia and liver cirrhosis. Also noteworthy is that significantly reduced agglutinin activities were reported in patients undergoing an antibiotic regimen [V. Boccardi et al., Vox Sang, 27, 268, (1974) and K. Fraser, J. Pathological Bacteriology, LXX, 13, (1955)].

Recently, it was observed and reported that anti-T could serve as a useful marker for the diagnosis of carcinoma because depressed levels of anti-T were found in sera from individuals diagnosed as having a malignant disease [Springer et al., Clin. Immunol. Immunopath., 7, 426, (1977)]. In particular, the serum anti-T agglutinin levels were reported to be severely depressed among patients diagnosed to have breast carcinoma or gastrointestinal carcinoma. Those studies detecting a correlation between depressed levels of anti-T and malignant disorders were conducted by a hemagglutination procedure. Specifically, normal human red cells treated with an enzyme (neuraminidase) expose T-antigens on their surface and thereby become T-antigen-bearing red cells. These red cells will agglutinate when anti-T "agglutinating" antibodies are present in the assay system. The degree of agglutination is semi-quantitative in evaluating the antibody levels.

While attempting to duplicate the published results by employing radio-immunoassay techniques, an inconsistency was discovered. Specifically, it was found that the total serum anti-T levels were significantly elevated in samples obtained from untreated cancer patients compared with those of controls secured from normal, healthy individuals and from subjects with benign pathological diseases.

The apparently inconsistent results have been reconciled by recognizing that not all anti-T antibodies are agglutinating antibodies. The non-agglutinating anti-T antibodies would not agglutinate with the T-antigen-bearing red cells and would, therefore, go undetected in the hemagglutination assay medium. The invention disclosed and claimed herein relies on sensitive and specific immunoassays which can detect all the anti-T antibodies, agglutinating and non-agglutinating, to thereby demonstrate that "total" serum anti-T antibody levels are signficantly elevated in cancer patients when compared with "total" anti-T antibody levels observed in normal, healthy donors and patients with benign pathological diseases.

SUMMARY OF THE INVENTION

Accordingly, it is the purpose of this document to disclose and demonstrate a method for the diagnosis of cancer which comprises immunochemically detecting elevated anti-T antibody activity in a biological sample from an untreated individual afflicted with a malignant disorder.

DESCRIPTION OF THE PREFERRED EMBODIMENT

In order to prepare the reagents necessary for the immunochemical determination of anti-T antibody levels, it is necessary to secure purified T-antigen. A suitable quantity of T-antigen can be prepared from O, MM and O, NN red blood cells according to the detailed procedure described by Springer et al. [Biochemistry, 5, 325, (1966); G. F. Springer et al., Carbohydrate Research, 40, 183 (1975)].

The purified T-antigen can be labeled with a variety of markers commonly employed in immunochemical techniques including radio-isotopes, enzymes and fluorescent dyes. In the Examples set forth below, labeling the purified T-antigen was achieved by using radioactive iodine ($^{125}I$) in the insoluble lactoperoxidase method described by David and Reisfeld [Biochemistry, 13, 1014, (1974)]. Typically, 20 $\mu$g of purified T-antigen is labeled using 1.2 mCi of $Na^{125}I$.

The anti-T antibody used in the detailed Examples was generated in rabbits by two separate methods. One group of animals was immunized with enzyme (neuraminidase)-treated human red blood cells and another with purified T-antigen mixed with complete Freund's adjuvant. The former group received 0.25 ml packed red cells and the latter group received 6–100 $\mu$g T-antigen in each injection until the immune response reached maturation. After three weeks following the injections, the rabbits were bled. The immunoglobulin fraction of the rabbit antisera was obtained by precipitation in 50% saturated $(NH_4)_2SO_4$ and subsequent washing with more of the same salt solution.

To reliably demonstrate the claimed method for diagnosing malignant conditions, it is necessary that the biological sample, e.g. sera or pleural fluid, be obtained from untreated patients. It has been observed in a series of serum samples obtained from clinically diagnosed cancer patients before, during and after treatment (surgery, chemo-, radio-, and hormonal therapy) that in some patients the serum anti-T levels were significantly altered after initiation of a therapy.

EXAMPLE I

DETERMINATION OF ANTI-T BY SOLID-PHASE COMPETITIVE RADIOIMMUNOASSAY (SPRIA)

Polystyrene tubes (13 × 100 mm) were coated with immunoglobulin solution containing a high concentration of rabbit anti-T antibodies. The coating solution was prepared in 0.01 M Tris, pH 9.0, buffer and the final protein concentration was adjusted to yield the absorbance reading (at 280 nm) of 0.022–0.024. After introducing 1.1 ml of the antibody coating solution into each tube, the tubes were allowed to stand overnight (~16 hrs.) at 4° C. They were washed twice with 0.01 M Tris, 0.15 M NaCl (Tris-saline) pH 7 buffer solution prior to use.

Serum samples were pre-diluted with 0.01 M phosphate buffered—0.15 M saline (PBS) before initiating the assay procedure. Specifically, 25 μl of serum was diluted with 1.0 ml PBS solution.

To begin the SPRIA procedure, 0.5 ml of 5 mg/ml bovine serum albumin (BSA) in PBS was introduced into each anti-T coated tube. One aliquot (100 μl) of the pre-diluted serum sample was pipetted into the tube, followed by a pre-diluted, constant volume (100 μl) of radiolabeled T-antigen ($^{125}$I-T), 250,000–300,000 counts per min/0.1 ml. A sufficient quantity of PBS solution was then added to bring the final volume of the mixture to 1.0 ml. The composition was mixed on a vortex mixer and incubated for 18 hours at 4° C. without disturbance. After incubation, the contents were aspirated and the tubes washed twice with 1.5 ml each of Tris-saline buffer. The tubes were counted on a gamma-counter to measure the amount of $^{125}$I-T bound to the immobilized anti-T antibodies. A standard curve had been constructed using serially diluted known sample. The anti-T levels of unknown samples were evaluated from the radioactivity corresponding to the standard curve.

Table I illustrates the correlation between anti-T antibody activity determined by the solid-phase RIA method described above and various malignant conditions. A reading was designated as elevated and positive when the anti-T activity reached 25 units or higher.

TABLE I

| ANTI-T ANTIBODY ACTIVITY MEASUREMENT BY SOLID-PHASE RADIOIMMUNOASSAY | | |
|---|---|---|
| Clinical Diagnosis | No. Positive/Total No. | % Positive |
| Normal healthy donors | 3/23 | 13 |
| Ca colon and rectum | 16/16 | 100 |
| Ca breast | 28/33 | 85 |
| Other Ca | 16/16 | 100 |
| Benign, non-cancerous disease | 14/51 | 27 |

The following example will demonstrate an alternate immunochemical procedure which will also detect elevated anti-T antibody levels consistent with the claimed phenomenon.

EXAMPLE II

IMMUNE-COMPLEX PRECIPITATION RIA

Serum samples were diluted (1:200) with PBS solution. Specifically, 10 μl of a serum sample was diluted with 2.0 ml PBS. A batch of disposable glass tubes (10×75 mm) were labeled and 100 μl of 0.5 mg/ml BSA in PBS was introduced into each tube. An aliquot (50 μl) of the pre-diluted serum sample was pipetted into the tube. Iodine labeled-T antigen solution was prepared by diluting $^{125}$I-T with 0.5 mg/ml BSA, PBS solution so that a radioactivity count of 100,000–120,000 counts/min./0.1 ml was attained. A sufficient amount of PBS solution was then added to make the final sample volume 0.30 ml. The contents were mixed on a vortex mixer and incubated overnight at 4° C. Following the incubation, an equal volume (0.30 ml) of $(NH_4)_2SO_4$ solution which was saturated at 23° C. was added and the mixture allowed to equilibrate for 30 min. at 4° C. The samples were then centrifuged at 1300× g for 30 min. at 4° C. The supernatant was decanted gently without disturbing the precipitate. The precipitates, including $^{125}$I-T anti-T antibodies, remained adhered at the bottom of the tube and were counted on a gamma-counter. A dose response curve obtained with serially diluted known samples served as a standard. The anti-T levels of unknown samples were evaluated from their radioactivity corresponding to the standard curve.

Table II illustrates the correlation between anti-T antibody activity determined by the immunoassay described in Example II and various malignant conditions. A reading was designated as elevated and positive when the anti-T activity reached 90 units or higher.

TABLE II

| ANTI-T ANTIBODY ACTIVITY MEASUREMENT BY FARR RADIOIMMUNOASSAY | | |
|---|---|---|
| Clinical Diagnosis | No. Positive/Total No. | % Positive |
| Normal healthy donors | 1/38 | 3 |
| Ca colon and rectum | 11/13 | 85 |
| Ca breast | 29/35 | 83 |
| Other Ca | 6/14 | 43 |
| Benign, non-cancerous disease | 3/47 | 6 |

Of course, numerous modifications and variations demonstrating the claimed phenomenon will occur to those skilled in the art; however, subsequent elaborations should not be interpreted as limiting the scope or application of the appended claims. Specifically,

What is claimed is:

1. A method of diagnosing cancer which comprises immunochemically detecting elevated anti-T antibody activity in a biological sample from an untreated individual.

2. A method according to claim 1 in which the biological sample is human serum.

3. A method according to claim 1 in which the biological sample is pleural fluid.

4. A method according to claim 1 which employs a radioimmunoassay.

5. A method according to claim 1 which employs radiolabled T-antigen.

6. A method according to claim 1 which employs a solid phase immunoassay system.

7. A method according to claim 1 which employs an immune-complex precipitation system.

8. A method of diagnosing cancer by detecting elevated levels of anti-T antibody which comprises:
mixing a biological sample from a therapeutically untreated individual with a known amount of labeled T-antigen and anti-T antibody affixed to a solid support;
allowing the affixed antibody to compete with any anti-T antibody in said sample and selectively complex with the labeled T-antigen;
separating the solid support from the reaction medium;
measuring the degree of binding of the labeled T-antigen with the affixed anti-T antibody; and
determining the amount of anti-T antibody present in said sample by comparing the degree of binding to a standard curve.

* * * * *